US010345265B2

(12) United States Patent
Stockdale et al.

(10) Patent No.: US 10,345,265 B2
(45) Date of Patent: Jul. 9, 2019

(54) WATER IMMERSIBLE DETECTOR

(71) Applicant: ION SCIENCE LIMITED, Cambridge Cambridgeshire (GB)

(72) Inventors: Mark Stockdale, Cambridge (GB); William Dean, Cambridge (GB)

(73) Assignee: ION SCIENCE LIMITED, Cambridgeshire (GB)

( * ) Notice: Subject to any disclaimer, the term of this patent is extended or adjusted under 35 U.S.C. 154(b) by 135 days.

(21) Appl. No.: 15/564,508

(22) PCT Filed: Mar. 24, 2016

(86) PCT No.: PCT/IB2016/051693
§ 371 (c)(1),
(2) Date: Oct. 5, 2017

(87) PCT Pub. No.: WO2016/162773
PCT Pub. Date: Oct. 13, 2016

(65) Prior Publication Data
US 2018/0080900 A1 Mar. 22, 2018

(30) Foreign Application Priority Data

Apr. 10, 2015 (GB) .................................. 1506150.0

(51) Int. Cl.
G01N 27/66 (2006.01)
G01N 33/18 (2006.01)
(52) U.S. Cl.
CPC ......... G01N 27/66 (2013.01); G01N 33/1826 (2013.01); G01N 2291/0253 (2013.01)

(58) Field of Classification Search
CPC ..................................................... G01N 27/66
See application file for complete search history.

(56) References Cited

FOREIGN PATENT DOCUMENTS

DE 202004000570 U1 3/2004
EP 1474681 B1 9/2007
(Continued)

OTHER PUBLICATIONS

Intellectual Property Office, Patents Act 1977: Search Report under Section 17 of Intellectual Property Office, Patent Application No. GB1506150.0, dated Jun. 4, 2015.
(Continued)

Primary Examiner — Lisa M Caputo
Assistant Examiner — Alex T Devito

(57) ABSTRACT

An apparatus for detecting the presence of gaseous analytes in water includes a submersible housing enclosing a water proof sensing chamber having a first wall made of a material transparent to UV light and a second wall formed by a gas permeable membrane for admitting into the sensing chamber gas dissolved in water in which the housing is immersed during operation, a first and a second spaced sensing electrodes disposed within the sensing chamber, and a circuit connected to the sensing electrodes for measuring a current flowing through the sensing electrodes on account of ionization of a gas in the sensing chamber by UV light. A third electrode is positioned in the sensing chamber, and the circuit is operative to apply a voltage across the third electrode and the first sensing electrode, the voltage being of sufficient magnitude to reduce condensation within the sensing chamber by hydrolyzing any droplet of condensation in electrical contact with the first and third electrodes.

20 Claims, 1 Drawing Sheet

(56) References Cited

FOREIGN PATENT DOCUMENTS

| EP | 2458375 A1 | 11/2011 |
|----|------------|---------|
| GB | 2328789 A  | 3/1999  |
| GB | 2449664 A  | 12/2008 |
| GB | 2527867 B  | 6/2016  |
| JP | 2002148240 A | 5/2002 |
| WO | 03046535 A2 | 6/2003 |

OTHER PUBLICATIONS

Chriswell C D et al, "Use of electrolytically generated hydrogen as a purge gas for the isolation of volatile organic compounds from groundwater", Separation Science & Technology, vol. 28, No. 15/16, Nov. 1993, pp. 2377-2386.

Patent Cooperation Treaty, International Search Report, Patent Application No. PCT/IB2016/051693, dated Jul. 20, 2016.

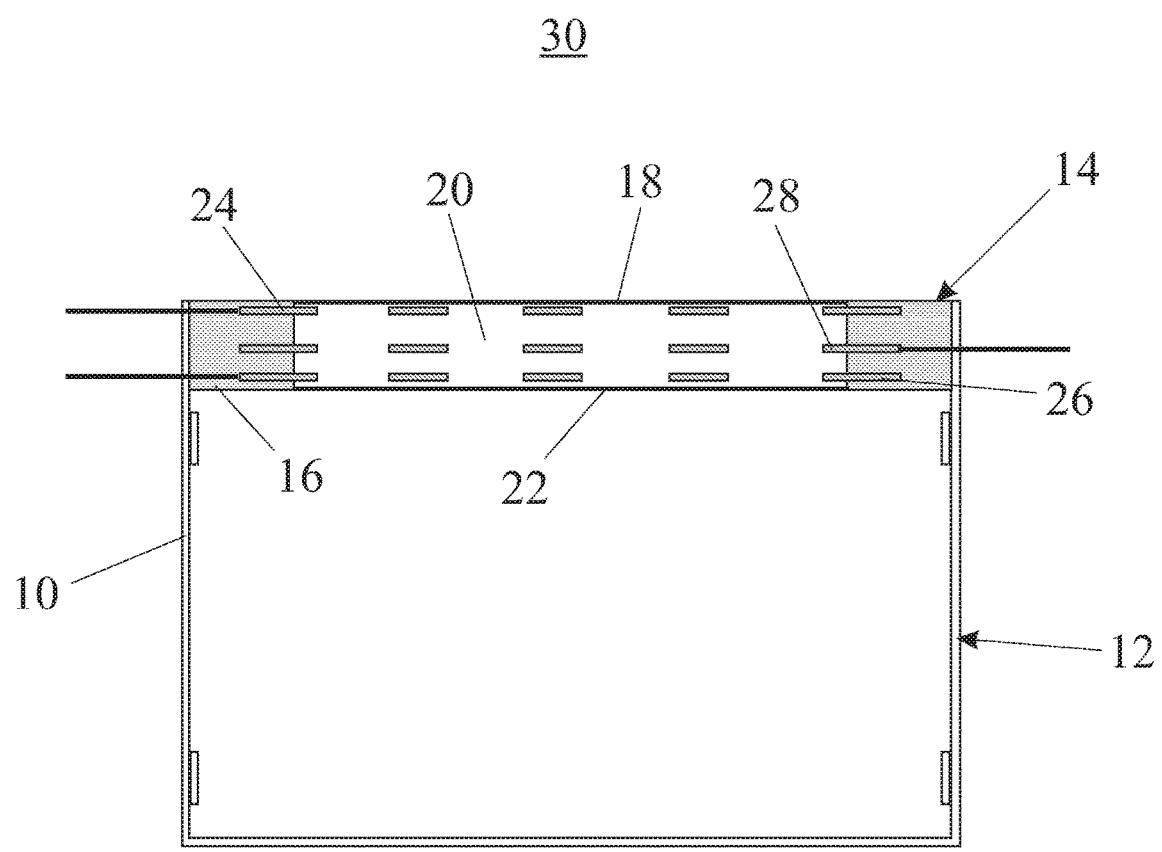

WATER IMMERSIBLE DETECTOR

FIELD OF THE INVENTION

This invention relates to detection of gaseous and volatile analytes dissolved in water and other aqueous fluids using a detector within which such materials are sensed in the gaseous phase. Analytes of particular interest are volatile organic compounds (VOC's) as found in water and aqueous solutions in concentrations varying from less than a part per billion (ppb, $10^{-9}$) to parts per thousand (ppt, $10^{-3}$) by mass.

BACKGROUND OF THE INVENTION

There is a need to detect and measure the presence of volatile compounds in natural and artificially contained sources of water, and in other aqueous fluids. Many such compounds are classed as volatile organic compounds, VOC's, and include irritants, oestrogens, carcinogens and other chemicals harmful to humans, animals and plant life. They are a matter of concern in marine environments, waterways, harbours, industrial process water, and waste water. They may also be of significance in other aqueous fluids such as in the detection of alcohols due to fermentation of liquid food stuffs and in brewing.

It is frequently of interest to search for the presence of gaseous species within large expanses of water, and to trace their source and extent in near real time, as for example may arise from spillage of petrochemicals into sea water. Such bodies of water are also subject to currents and drift. Therefore it is preferable for sensors which are able to detect target analytes in water to provide a fast and quantitative measurement of their concentration.

It should be noted that clean potable water contains very low or imperceptible concentrations of any VOC's, whilst polluted waters may contain any of a wide suite of VOC's. Therefore VOC in water detectors may be of most service in rapidly identifying the presence of a suite of different analytes in water, so as to identify the source of VOC's confidently before they disperse, and enable a select few samples of water to be retrieved for less time critical and more costly detailed analysis. A detector used in this way is commonly known as a screening tool.

One class of such sensors or detectors contain a membrane, typically hydrophobic, providing a barrier between the aqueous sensed environment and a detector enclosure, through which the analyte is able to diffuse. In GB Patent Application GB1421306.0, which is incorporated herein by reference, one such detector, having as one member a gaseous enclosure is located within a few millimeters of a preferably hydrophobic and porous membrane separating it from water prospectively containing VOC's. The detector is claimed to provide a response to VOC's in water at some gas equilibrated concentration.

The present invention concerns the operation and configuration of a photoionisation detector for the detection of volatiles in water.

One problem that can be presented to sensors of volatile in water sensors such as in GB1421306.0 is that of condensation. A volatile in water sensor may be plunged from a relatively cold air or watery environment into water which is significantly warmer. In such circumstances water vapour in gas at the liquid interface of the sensor membrane is warm and at a saturated vapour concentration. On free diffusion through a porous membrane into the cold sensor interior, the water laden air is cooled to a temperature below its dew point, causing water condensation within the sensor. After many fluctuations in temperature the water in the sensor gaseous cavity may accumulate to such an extent as to cause the sensor to fail.

The present invention seeks to mitigate the above mentioned problem and therein extend the time over which a volatile in water sensor can operate within water.

SUMMARY OF THE INVENTION

According to the present invention, there is provided apparatus for detecting the presence of gaseous analytes in water, as set forth in claim 1 of the appended claims.

It is preferable for the difference in electrical potential across two sensing electrodes to be at least 2V and for the distance between them to be 2 mm or less. In the case of a photoionisation detector, it is preferable for the electric potential difference between the primary cathode and anode to be at least 100V per mm of spacing between them.

It is advantageous for a spacer separating the primary and secondary electrodes to compromise a low dielectric and water repellent material such as polytetrafluoroethylene (PTFE).

BRIEF DESCRIPTION OF THE DRAWING

The invention will now be described further by way of example with reference to the accompanying drawing in which the single FIGURE is a schematic diagram of a photoionisation detector (PID) for use under water.

DETAILED DESCRIPTION OF THE DRAWING

Hereinafter for convenience an electrode at which negative ions are attracted and neutralised, at which hydrogen may also be generated due to the electrolysis of water, will be referred to as a cathode, and an electrode to which positive ions are attracted, and at which oxygen may also be generated as a consequence of the electrolysis of water, shall be referred to as an anode.

Turning now to FIG. 1, the schematic representation shows a section through a PID cell 14. The PID cell is similar to that of GB 2449664, which is incorporated herein by reference, in that it contains a UV light source 12 arranged adjacent a gas sensing chamber 20 and separated by means of a UV transparent window 22.

Inside the chamber 20 is a stack of at least three electrodes, consisting of a pair of sensing electrodes, 24 and 26, and a third electrode 28, referred to here, as the fence electrode. The fence electrode is sandwiched between the first and second sensing electrodes, the first sensing electrode (cathode) 24 being furthest from the UV light source and the second sensing electrode (anode) 26 being adjacent the window 22 separating the light source from the sensing chamber.

The illustrated apparatus, like that of GB1421306.0, differs from GB 2449664 in that the PID cell is adapted for use in submerged situations. The sensing chamber 20 is sealed from the sample liquid 30 by means of a, preferably hydrophobic, gas permeable membrane 18. As described in GB1421306.0, the membrane allows an analyte in the sensing chamber 20 to reach near equilibrium with the concentration of the analyte in the adjoining liquid phase of the sample liquid 30.

The PID then measures the concentration of analyte inside the sensing chamber 20, which is indicative of the concentration of analyte in the sample liquid 30 by virtue of the equilibrium condition. The mechanism by which the PID measures the analyte concentration is essentially the same as when used in non-submerged conditions and need not therefore be described in further detail in the present context In addition, the electrodes (24,26,28) may be supported and separated by spacers made of a low dielectric hydrophobic material such as polytetrafluoroethylene. This forms a substantial portion of the walls of the sensing chamber 20 and serves to reduce the wetting effect of condensation. Wetting of the walls should be avoided since it permits conduction of currents between the sensing electrodes negatively impacting the accuracy of the sensor.

The purpose of the fence electrode, when used in previous, non submerged conditions, is documented in EP 1474681, which is incorporated herein by reference. To summarise, it is concerned with removing from the current sensed by the sensing electrodes, additional currents that result from mechanisms within the PID cell other than photoionisation.

The use of a third "fence" electrode was not previously contemplated for dissolved VOC detection, as until recently, PIDs were not utilised in submerged conditions to detect the concentration of dissolved VOC's in water.

In use the potential difference between the sensing electrodes 24 and 26 is approximately 200V. The third "fence" electrode sits at the substantially same potential as the anode 26 such that no current flows between them.

When used under water, as described above, the interior of the sensing chamber can suffer the effects of condensation to the detriment of the working life of the sensor. Whereas in applications where a PID detector is used to detect VOC's in air, the fence electrode serves simply to shield the sensing electrode from the effects of condensation collecting on the walls of the sensing chamber, its purpose in a water immersible detector is to prevent such condensation. In particular, by virtue of the potential difference between the fence electrode 28 and the first sensing electrode (cathode) 24, any water in electrical contact with both electrodes is hydrolysed into hydrogen and oxygen, removing the water as a contaminant of the sensing chamber 20.

When not immersed in water, the degree of condensation in a PID 14 is less problematic, and any hydrolysis that may occur is de minimis as the current that flows through the fence eletrode is typically less than one microamp. By contrast, in a preferred embodiment, the applicants have sought to increase the power handling capacity of the fence electrode such that it is capable of hydrolysing the larger quantities of water that affect the PID 14 when used in under water conditions.

The fence electrode is used to intercept current that may flow across contaminated walls inside the PID cell. This is particularly useful on occasions of PIDs being exposed to salty environments and to analytes which deposit salts as products of photo-ionisation and photo-dissociation. When a PID sensor is used in air, accommodating a lamp of 6 mm diameter, a fence current threshold of typically 0.3 μA is sufficient to uptake wall currents caused by this form of contamination, ensuring that the sensing electrode selectively senses the current generated within the photoionisation cavity itself.

Upon the immersion of the PID in water, it is desirable to increase this current threshold 1000-fold (300 μA) to enable the fence electrode to neutralise the effect of the electric current arising from conductive PID cavity wall surfaces, so as to enable the current caused by photoionisation to be accurately determined. At this current, water can be consumed quite rapidly and the cell is dried out over time. Of course any current limit in excess of the conventional 0.3 μA for the use of a PID with a fence electrode in air, will produce proportionally beneficial results with regard to the hydrolysis of water within the sensor. Increasing degrees of success have been achieved at 0.05 mA, 0.1 mA and 0.2 mA.

A cathode provided for the electrolysis of water and therefore engaged in half cell reactions such as $$2H^+ \text{ (aqueous)} + 2e = H_2 \text{ (gas)}$$

may, intentionally or otherwise, be also engaged in other reactions, including, without limitation, the reduction of cations within a saline fluid formed by for example the dissolution or deliquescence of salts precipitated on wall members which form part of the gaseous cavity abutting the cathode, or in the reduction of oxygen dissolved in the aqueous fluid.

Correspondingly, an anode provided for the electrolysis of water, and which may thus be engaged in half cell reactions such as $$H_2O = \tfrac{1}{2}O_2 + 2H^+ + 2e$$

may, be also engaged in other reactions including without limitation, the oxidation of anions within a saline fluid formed by for example the dissolution or deliquescence of salts precipitated on wall members which form part of the gaseous cavity abutting the anode, in the removal of gas borne electrons, such as may arise from photo-ejection from a cathode exposed to photons and propelled therefrom towards the anode.

The invention claimed is:

1. An apparatus for detecting the presence of gaseous analytes in water, comprising:
   a submersible housing enclosing a water proof sensing chamber having a first wall made of a material transparent to UV light and a second wall formed by a gas permeable membrane for admitting into the sensing chamber gas dissolved in water in which the housing is immersed during operation,
   a first and a second spaced sensing electrodes disposed within the sensing chamber, and
   a circuit connected to the sensing electrodes for measuring a current flowing through the sensing electrodes on account of ionisation of a gas in the sensing chamber by UV light,
   wherein a third electrode is positioned in the sensing chamber and the circuit is operative to apply a voltage across the third electrode and the first sensing electrode, the voltage being of sufficient magnitude to reduce condensation within the sensing chamber by hydrolysing any droplet of condensation in electrical contact with the first and third electrodes.

2. The apparatus as claimed in claim 1, wherein the distance between the first and second sensing electrodes is 2 mm or less.

3. The apparatus as claimed in claim 1, wherein the potential difference between the first and second sensing electrodes is at least 100V per mm of spacing between the first and second sensing electrodes.

4. The apparatus as claimed in claim 1, wherein the potential difference between the second and third electrodes is substantially zero.

5. The apparatus as claimed in claim 1, wherein the first sensing electrode is a cathode and the second sensing electrode is an anode.

6. The apparatus as claimed in claim 1, wherein a spacer separating the first and second sensing electrodes is made of a low dielectric and water repellent material.

7. The apparatus as claimed in claim 1, wherein the current flowing capacity of the first and third electrodes is 300 µA.

8. The apparatus as claimed in claim 1, wherein the distance between the first and second sensing electrodes is 2 mm or less and the potential difference between the first and second sensing electrodes is at least 100V per mm of spacing between the first and second sensing electrodes.

9. The apparatus as claimed in claim 8, wherein the potential difference between the second and third electrodes is substantially zero.

10. The apparatus as claimed in claim 9, wherein the first sensing electrode is a cathode and the second sensing electrode is an anode.

11. The apparatus as claimed in claim 10, wherein a spacer separating the first and second sensing electrodes is made of a low dielectric and water repellent material.

12. The apparatus as claimed in claim 10, wherein the current flowing capacity of the first and third electrodes is 300 µA.

13. The apparatus as claimed in claim 1, wherein the distance between the first and second sensing electrodes is 2 mm or less and the potential difference between the second and third electrodes is substantially zero.

14. The apparatus as claimed in claim 13, wherein the first sensing electrode is a cathode and the second sensing electrode is an anode.

15. The apparatus as claimed in claim 14, wherein a spacer separating the first and second sensing electrodes is made of a low dielectric and water repellent material.

16. The apparatus as claimed in claim 13, wherein the current flowing capacity of the first and third electrodes is 300 µA.

17. The apparatus as claimed in claim 1, wherein the potential difference between the first and second sensing electrodes is at least 100V per mm of spacing between the first and second sensing electrodes and the potential difference between the second and third electrodes is substantially zero.

18. The apparatus as claimed in claim 17, wherein the first sensing electrode is a cathode and the second sensing electrode is an anode.

19. The apparatus as claimed in claim 18, wherein a spacer separating the first and second sensing electrodes is made of a low dielectric and water repellent material.

20. The apparatus as claimed in claim 6, wherein the low dielectric and water repellent material comprises polytetrafluoroethylene.

\* \* \* \* \*